United States Patent [19]
Schultz et al.

[11] 4,421,246
[45] Dec. 20, 1983

[54] BIOLOGICAL TISSUE CASSETTE

[75] Inventors: Ronald W. Schultz; Donald R. Graham, both of Pittsburgh, Pa.

[73] Assignee: Allied Corporation, Morris Township, Morris County, N.J.

[21] Appl. No.: 390,301

[22] Filed: Jun. 21, 1982

[51] Int. Cl.³ .................... B65D 39/00; B65D 41/13
[52] U.S. Cl. .................... 220/307; 206/565; 206/820; 206/205; 220/306; 220/375; 220/8; 220/355
[58] Field of Search ............... 220/307, 306, 355, 375, 220/23.8, 8; 206/820, 565, 205

[56] References Cited

U.S. PATENT DOCUMENTS

| | | | |
|---|---|---|---|
| Re. 28,165 | 5/1974 | McCormick | 425/117 |
| 2,825,450 | 3/1958 | Lambert | 220/23.8 |
| 3,031,111 | 4/1962 | Stull | 220/375 |
| 3,034,884 | 7/1962 | White | 220/306 |
| 3,164,250 | 1/1965 | Paxton | 206/820 |
| 4,220,252 | 9/1980 | Beall et al. | 220/307 |

*Primary Examiner*—William T. Dixson, Jr.
*Attorney, Agent, or Firm*—Webb, Burden, Robinson & Webb

[57] ABSTRACT

A tissue cassette which includes an open-topped, perforated base member adapted to receive a tissue specimen, a perforated lid member adapted to cover the base member and be secured thereto in a closed position, and one or more gates joining the lid members to the base member in an open position wherein the gates will break when flexed.

21 Claims, 8 Drawing Figures

BIOLOGICAL TISSUE CASSETTE

DESCRIPTION

1. Technical Field

This invention relates to a tissue cassette and more particularly to a tissue cassette suitable for holding a biological tissue specimen while it is being treated with fluids and for holding embedded tissue in a microtome while the tissue is sliced into sections for microscopic examination.

2. Background Art

Processes for examining thin slices of a biological tissue under a microscope are well known in the art. In one process, the tissue specimen is treated with several different fluids and then the specimen is embedded in a block of paraffin wax for slicing by a microtome. The slice specimen is placed on a slide for microscopic examination.

Apparatus for holding such a tissue specimen during the fluid treatment and paraffin embedding, referred to generally as tissue cassettes, are known in the art. U.S. Pat. No. Re. 28,165 describes one tissue cassette which includes an open mold or base member with a perforated bottom for holding the tissue specimen and a separate, removable, perforated cover or lid for the base member. The tissue specimen is placed in the base member and the lid is positioned on the base for processing the specimen with the desired fluids. However, this tissue cassette has the disadvantage that the removable lid is preferably made from a metal, while the base is made from a plastic, necessitating the manufacture and subsequent handling of the base and lid as two separate articles. U.S. Pat. No. 4,034,884 shows a similar two-part tissue cassette with plastic, adjustable height lid.

U.S. Pat. No. 4,220,252 eliminates the disadvantages of a two-part tissue cassette by joining the lid to the base with a frangible hinge portion which permits closure of the cassete without breaking the hinge. The hinge is frangible because the base is utilized in the subsequent embedding of the specimen in paraffin and the lid must be removed once the processing of the tissue specimens with the fluids is completed. However, because the hinge portion must function as a hinge without breaking while the lid is rotated about the hinge and mated with the base, the hinge portion must be made of a material which is yieldable and has reasonably high flexural strength. Such a material is not readily broken and a significant amount of force is needed to separate the lid from the base after the processing of the tissue is completed. Because the tissue specimen and tissue cassette are generally quite small in size, the use of even a small amount of force could easily knock the tissue specimen out of the base.

Accordingly, it is an object of the present invention to provide a tissue cassette in which the lid and base members are joined together for ease of manufacture and handling but in which the lid and base may be readily separated from each other without disturbing the tissue specimen.

Often in the prior art tissue cassettes air becomes entrapped inside of the cassettes while the tissue specimen is being processed with the fluids. Such entrapped air may displace the tissue specimen or prevent the treating liquids from fully permeating the tissue specimen.

Accordingly, it is a further object of the present invention to provide a tissue cassette which allows air to flow from the interior of the cassette when the tissue specimen is being processed without becoming entrapped and also provides for improved fluid flow through the cassette.

DISCLOSURE OF THE INVENTION

Accordingly, I have invented a tissue cassette which includes an open-topped, perforated base adapted to receive a tissue specimen, a perforated lid adapted to cover the base and be secured thereto in a closed position, and one or more gates joining the lid to the base in an open position wherein the gates will break when flexed. The base is a rectangularly shaped structure with a perforated bottom and back and side walls extending upwardly therefrom along the outside edges, a front wall extending between the side walls, and a first angled wall connected to the front wall. The lid is a rectangularly shaped, perforated plate of substantially the same dimensions as the base. The base and lid include means for securing the two parts together in a closed position. In one embodiment, the front wall extends from the top edge of the side only a short distance downward, the perforated bottom terminates behind and beneath the front wall, and the perforated bottom includes a second angled wall connected along the front edge of the bottom and extending outwardly and upwardly toward but terminating short of the front wall, thereby forming an opening between the front wall and the second angled wall. In another embodiment the front wall is connected to the perforated bottom along the front edge of the bottom, extends upwardly to the top edge of the side walls, and includes a longitudinal slot therethrough. The tissue cassette is a preferably molded and unitary structure from a plastic material which has a low flexural modulus and a tendency to break when flexed and is also resistant to the chemicals which treat the tissue specimens.

BEST MODE FOR CARRYING OUT THE INVENTION

Figure 1:
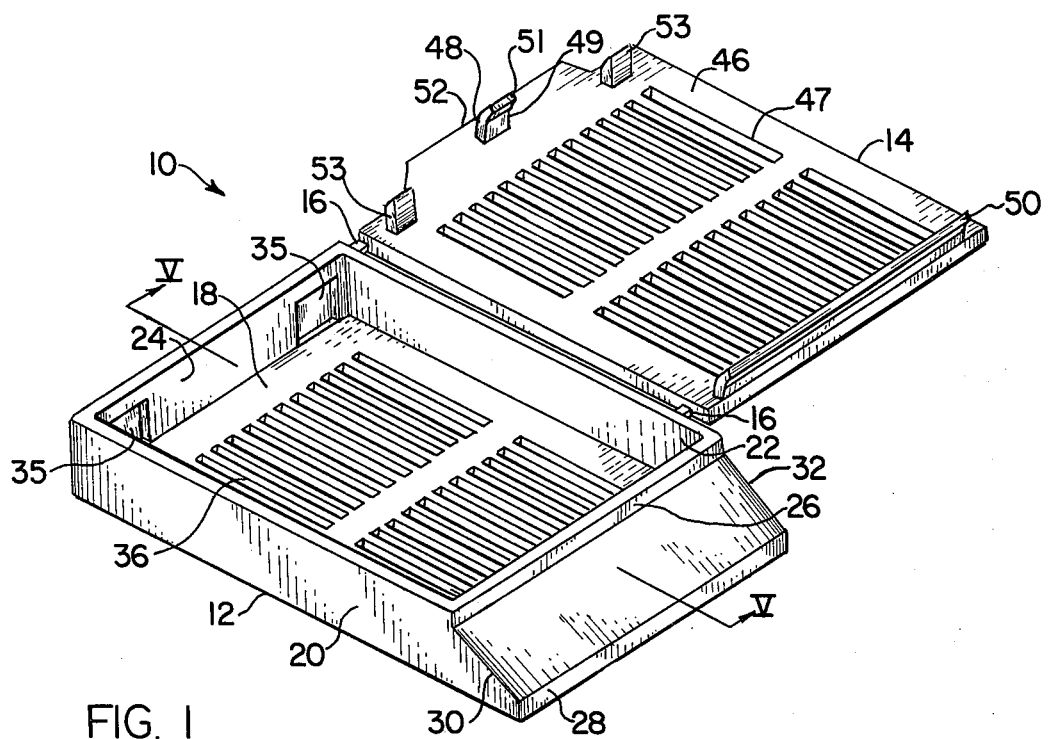
FIG. 1 is a perspective view of a tissue cassette in accordance with the present invention.

Disclosed herein are two different but related embodiments of a tissue cassette in accordance with the present invention. FIGS. 1-5 relate to a first embodiment of a tissue cassette and FIGS. 6-8 relate to a second embodiment. Rather than repeat the discussion of elements identical in both embodiments, like reference numbers will be used to refer to like elements throughout the drawings and the detailed description of the drawings.

Referring now to FIGS. 1–5, there is shown the first embodiment of a tissue cassette 10 in accordance with the present invention. The tissue cassette 10 includes an open-topped receptacle or base member 12 with a flat lid member 14 attached to the base 12 by one or more connecting gates 16.

The base 12 is rectangularly shaped with a flat bottom 18 and with opposed and parallel first and second side walls 20, 22 and a back wall 24 connected therebetween, all extending upwardly from and substantially perpendicular to the bottom 18 along its outer edges. A front wall 26 opposed and parallel to the back wall 24, is connected between the side walls 20, 22 but extends only a short distance down along the side walls 20, 22 from their upper edges toward the bottom 18. The front wall 26 forms a first lid retention means. A first or front angled wall 28 is connected to the bottom of the front wall 26 and extends downwardly and outwardly therefrom. The side walls 20, 22 extend outwardly beyond the front wall 26 and connect to the front angled wall 28 along its side edges 30, 32, respectively. The outer surface of the back wall 24 includes one or more rectangular recesses 34 which extend partially into the back wall 24 and form a second lid retention means. For illustrative purposes, only one recess 34 is shown in the figures. The inner surface of the back wall 24 includes one or more rectangular recessed slots 35, each of which extends partially into the back wall 24 and down through the bottom 18. For illustrative purposes, two slots 35 are shown. The slots 35 function as a drain through the bottom 18 when the tissue specimen is being processed with fluids.

The bottom 18 includes a plurality of openings or perforations 36 therethrough. These perforations 36 allow the fluids to pass through the tissue cassette 10 while the tissue specimen is being processed. While the perforations 36 are shown as narrow rectangular slots, it is to be understood that any size or shape may be utilized, such as a circle, triangle, or the like, provided that a perforation through any part of the tissue cassette 10 is smaller than any tissue sample placed in the base 12.

Figure 2:
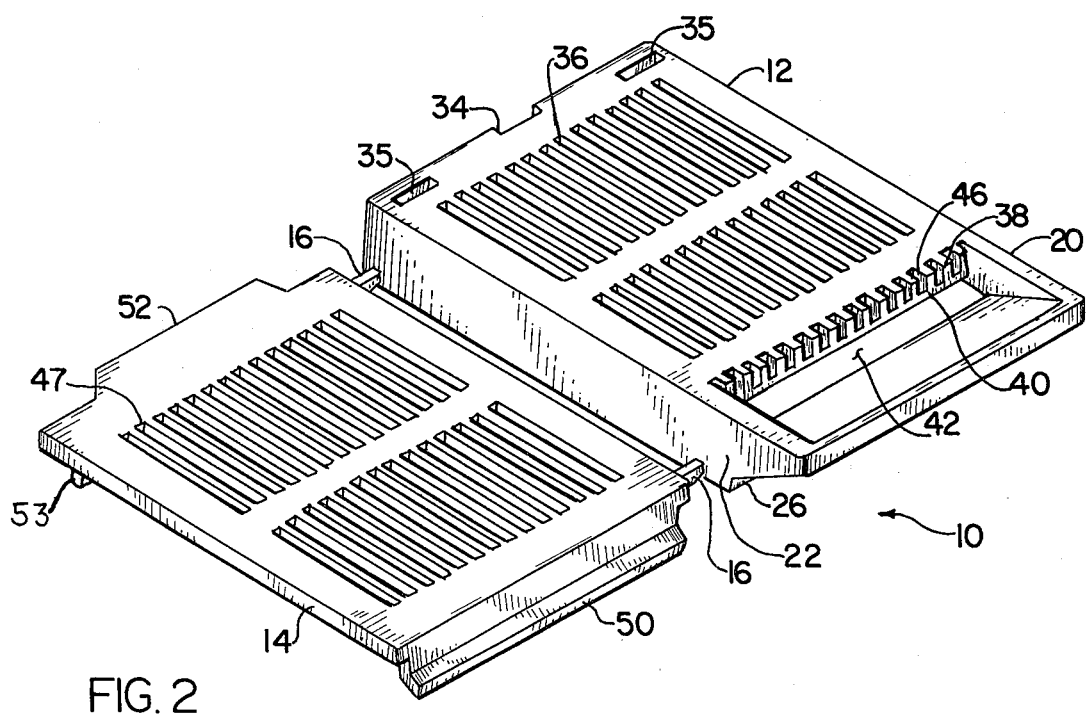
FIG. 2 is a perspective view showing the bottom of the tissue cassette of FIG. 1.
Figure 3:
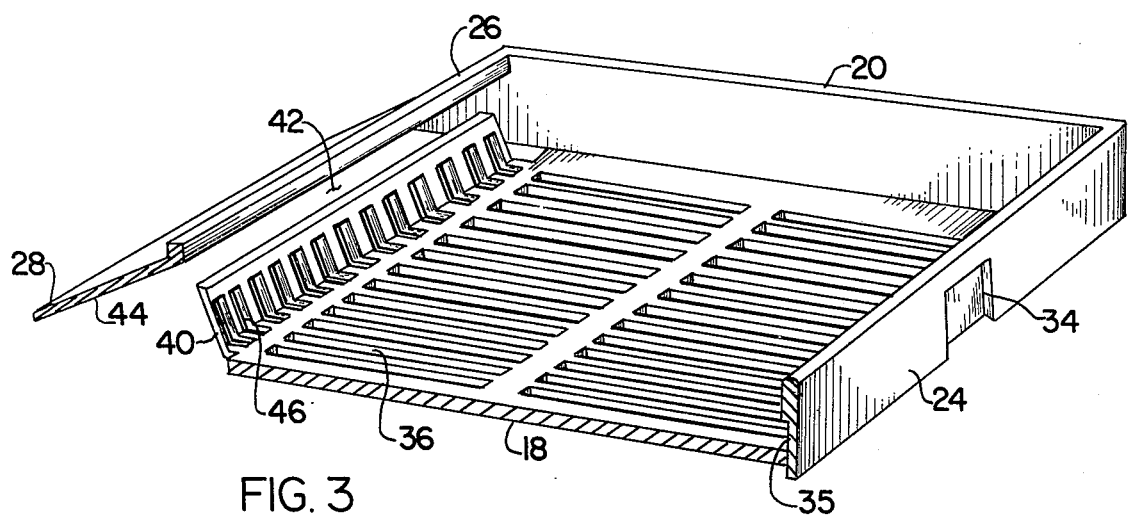
FIG. 3 is a perspective view of the tissue cassette of FIG. 1 with one side wall and the lid removed.
Figure 4:
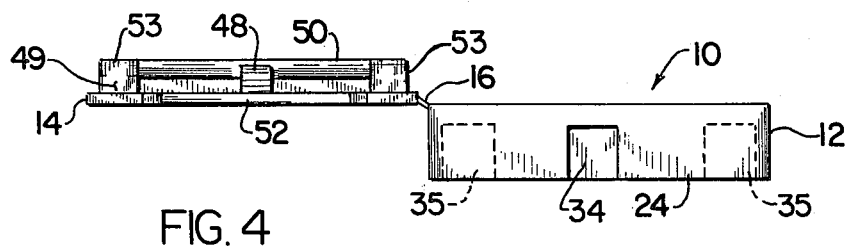
FIG. 4 is an end view of the tissue cassette of FIG. 1.

In the first embodiment, the bottom 18 does not extend completely to and connect with the front angled wall 28 but stops a short distance behind and beneath the front wall 26. An inner or second angled wall 40 is connected to the front edge 38 of the bottom 18 and extends outwardly and upwardly toward, but terminates short of, the front wall 26. The inner angled wall 40 may extend completely between and be connected to the side walls 20, 22 or may end a short distance from the side walls 20, 22 as shown in FIGS. 2 and 3. An opening 42 is formed between the front wall 26 and the inner angled wall 40 and provides a pathway for air to flow out from the interior of the base 12 and along the under surface 44 of the front angled wall 28 and prevents the entrapment of any air within the tissue cassette 10. The processing fluids may also flow out through the opening 42. The opening 42 must be large enough to receive the locking ridge 50 (described later) yet small enough to prevent the tissue specimen from floating out with the processing fluids. A plurality of perforations 46 are provided through the bottom 18 and the inner angled wall 40 in the vicinity of the front edge 38 where the bottom 18 and the inner angled wall 40 are joined which also allow the fluids to exit the tissue cassette 10.

The lid 14 is a flat, rectangularly shaped plate of the same approximate size as the area enclosed by the back wall 24, front wall 26 and side walls 20, 22 of the base 12. The lid 14 includes a pluality of perforations 47 similar to the perforations 36 in the bottom 18 of the base 12.

Figure 5:
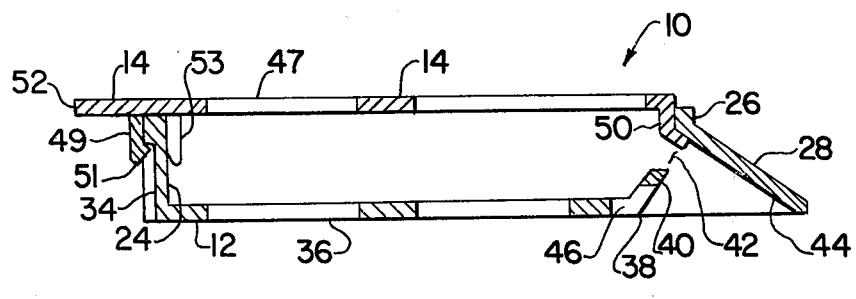
FIG. 5 is a section taken along line V—V in FIG. 1 with the lid positioned on the base.

The lid 14 includes a locking ridge 50 connected to its upper surface 46 and extending upwardly along its front edge to form a first lid locking means. Surface 46 is oriented upward when the tissue cassette 10 is in the open position. The locking ridge 50 has a cross section shaped like a "V" and is positioned on the lid 14 so that the "V" points outward. The locking ridge 50 is aligned with and matingly engages the front wall 26 when the lid 14 is snapped on the base 12 in the closed position as shown in FIG. 5.

The lid 14 also includes a handle 52 mounted along its back edge and coplanar with the lid 14. This handle 52 facilitates removal of the lid 14 from its closed position on the base 12 when the processing of a tissue specimen is complete.

Connected to the upper surface 46 of the lid 14 and extending upwardly along its back edge are one or more locking fingers 48 which form a second lid locking means. For illustrative purposes, one locking finger 48 is shown. The locking finger 48 includes a rectangularly shaped finger base portion 49 extending upwardly from the lid 14 with a frontwardly projecting ridge 51 connected to the top of the finger base portion 49. The locking finger 48 generally has an L-shaped cross section. The locking finger 48 is located on the lid 14 such that it is aligned with and matingly engages a corresponding recess 34 in the back wall 24 when the lid 14 is snapped into place on the base 12 in the closed position as shown in FIG. 5. Also connected to the upper surface 46 of the lid 14 and extending upwardly along its back edge are one or more guides 53. For illustrative purposes, two guides 53 are shown. The guides 53 are located on the lid 14 such that each is aligned adjacent the inner surface of the back wall 24 when the lid 14 is snapped on the base 12 as shown in FIG. 5. The guides 53 aid in aligning the lid 14 onto the base 12.

Figure 6:
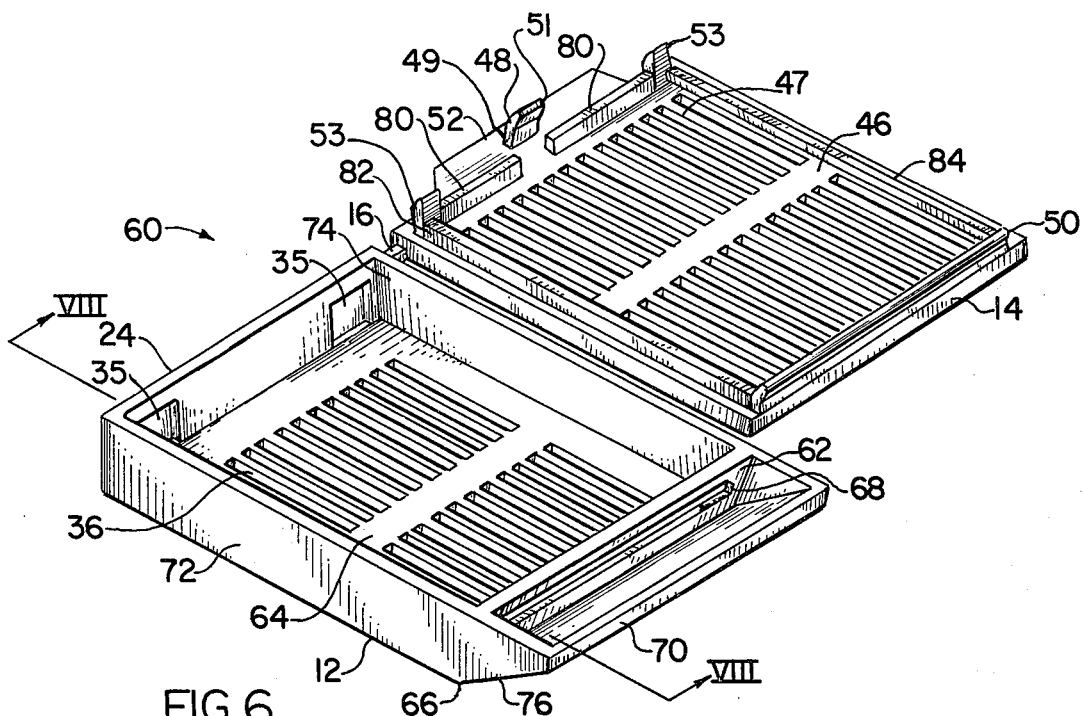
FIG. 6 is a perspective view of another embodiment of a tissue cassette in accordance with the present invention.
Figure 7:
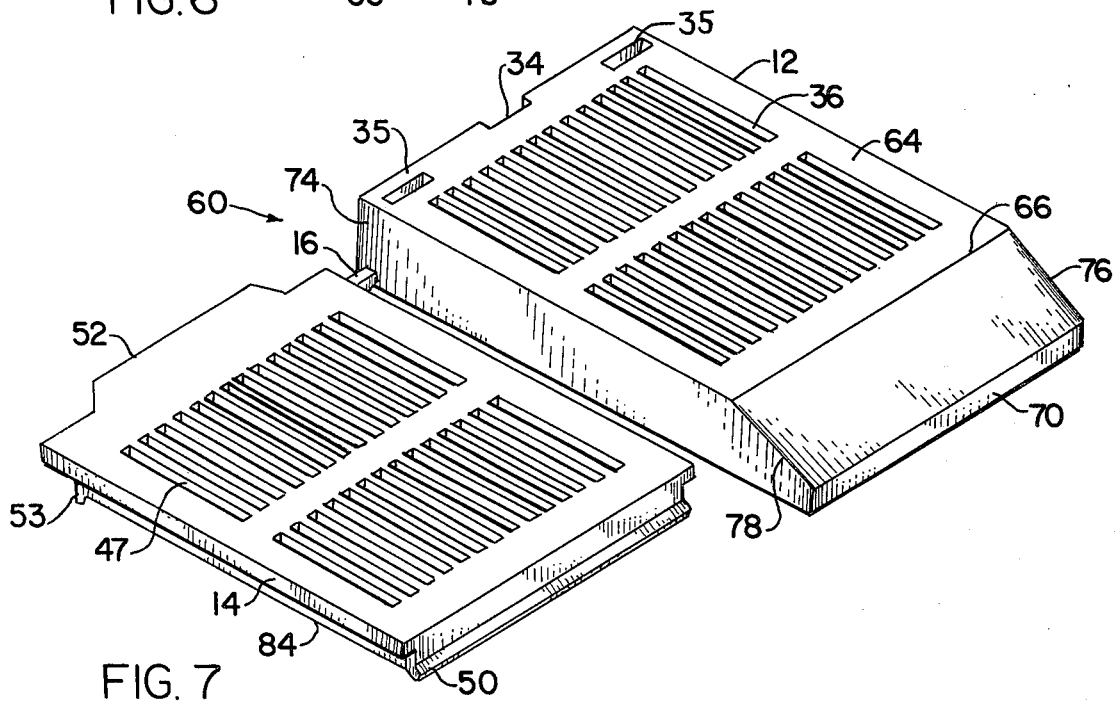
FIG. 7 is a perspective view showing the bottom of the tissue cassette of FIG. 6.
Figure 8:
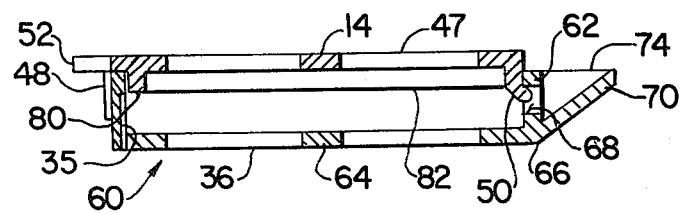
FIG. 8 is a section taken along line VIII—VIII in FIG. 6 with the lid positioned on the base.

Referring now to FIGS. 6–8, there is shown the second embodiment of a tissue cassette 60 in accordance with the present invention. In this embodiment, the front wall 62 is connected to the bottom 64 along the bottom front edge 66 and extends upwardly therefrom between and connected to the first and second side walls 72, 74 and opposed and parallel with the back wall 24. The bottom 64 extends completely between the front wall 62 and the back wall 24 and is connected thereto. The front wall 62 includes a narrow longitudinal slot 68 extending therethrough and parallel with the bottom 64 to form the first lid retention means. The locking ridge 50 mates with and engages the longitudinal slot 68 when the lid 14 is snapped on the base 12 in the closed position as shown in FIG. 8. The longitudinal slot 68 must be wide enough to receive the locking ridge 50 and be narrower than the size of the tissue specimens.

In the second embodiment, a first angled wall 70 is connected to the front wall 62 and bottom 64 along the front edge 66 of the bottom and extends upwardly and outwardly therefrom. The side walls 72, 74 extend outwardly beyond the front wall 62 and connect to the front angled wall 70 along its side edges 76, 78. Air may flow from the interior of the base 12 along the pathway through the longitudinal slot 68 and behind the first angled wall 70, thus preventing any air from becoming entrapped within the tissue cassette 60 while the tissue specimen is being processed with fluids.

The lid 14 may also include, in either embodiment, several small walls extending upwardly from and connected to its upper surface 46. As shown in FIGS. 6–8, the lid 14 includes a lid back wall 80 extending along the lid back edge between the guides 53, a first lid side wall 82 extending slightly recessed from and along one side edge of the lid 14 between one end of the locking ridge 50 and the opposite guide 53, and a second lid side wall 84 extending slightly recessed from and along the other side edge of the lid 14 between the other end of the locking ridge 50 and the opposite guide 53. The external dimensions of the area circumscribed by the lid back wall 80, the lid side walls 82, 84, and the lower portion of the locking ridge 50 immediately adjacent the lid 14 is slightly smaller than the inner dimensions of the area in the base 12 formed by the back wall 24, the front wall 62, and the side walls 73, 74 and permits the lid 14 to be snuggly mated onto the base 12 in the closed position with the lid walls 80, 82, 84 extending inwardly as shown in FIG. 8. The back wall 80 may extend completely between the guides 53 or may be broken in the vicinity of the locking finger 48 as shown in FIG. 6.

As shown in FIGS. 1, 2, 4, 6, and 7, the base 12 and the lid 14 are joined together in the open position by one or more breakable gates 16 which are formed between the lid 14 and base 12 during the manufacture process. The gates are provided to join the lid and the base physically together, requiring the handling of only one article prior to its use, and also to make the manufacture of the tissue cassette easier, requiring the use of only one mold. The gates 16 are shown in the figures located between the second side wall 22 or 74 and one edge of the lid 14. However, the gates 16 may be located at any convenient location provided the base 12 and lid 14 are physically joined together. While a plurality of gates 16 are preferred, as few as one gate 16 may be utilized as is shown in FIGS. 6 and 7.

The base, lid and gates of a tissue cassette in accordance with the present invention are preferably molded as a unitary structure from a thermosetting or thermoplastic material which when flexed will break rather than one which is yieldable and has high flexural strength. This is required in order that the gates can be easily broken by twisting the tissue cassette to detach the lid from the base. Preferably a thermoplastic material will be used in connection with the injection molding of the structure. Furthermore, the material must be resistant to the chemicals used to process the tissue specimen while at the same time have a low flexural modulus and a tendency to break when flexed. Suitable materials include homopolymers, copolymers, polyesters, nylon, polypropylene, polyethylene and fluoroplastics. A preferred material is an acetal copolymer.

The tissue cassette of the present invention is used in operation as follows: The lid 14 is first separated from the base 12 by twisting the lid in an opposite direction from the base and breaking the connecting gates 16. The tissue sample under test is placed inside the base 12, the locking ridge 50 is mated with the first lid retenion means, either the bottom of the front wall 26 or the longitudinal slot 68, and the locking finger 48, aided by the positioning of the guides 53, is snapped into the recess 34 in the back wall 24 of the base. The resulting structure, without the tissue specimen, is shown in cross section in FIGS. 5 and 8. When the conventional steps for processing the tissue specimen with the desired fluids are concluded, the lid 14 is removed from the base 12 by lifting upwardly on the handle 52. The base 12 is also utilized in the paraffin embedding processing to facilitate holding the embedded specimen during slicing.

The front angled wall (28 and 70) is provided with a textured outer surface so that an identification number of other designation may be written thereon with a pen or pencil and thus identify the particular tissue specimen under study.

Although the invention has been described with reference to particular materials and configurations, it is only to be limited so far as is set forth in the appended claims.

We claim:
1. A tissue cassette comprising:
   (a) an open-topped, perforated base member adapted to receive a tissue specimen,
   (b) a perforated lid member adapted to cover the base member and be secured thereto in a closed position, and
   (c) one or more gates joining the lid member to the base member in an open position wherein said gates will break when flexed.

2. The tissue cassette of claim 1 wherein the base is a rectangularly shaped structure with a perforated bottom and a back wall and a pair of opposed side walls all extending upwardly from and connected to the outside edges of the bottom, with a front wall extending between and connected to the side walls, and with a first lid retention means associated with the front wall and a second lid retention means in the back wall.

3. The tissue cassette of claim 1 wherein the lid is a rectangularly shaped, perforated plate with a first lid locking means connected to the lid upper surface along its front edge and a second lid locking means connected to said upper surface along its back edge.

4. The tissue cassette of claim 1 wherein:
   (a) the base is a rectangularly shaped structure with a perforated bottom, and a back wall and a pair of opposed side walls all extending upwardly from and connected to the outside edges of the bottom, with a front wall extending between and connected to the side walls, and with a first lid retention means associated with the front wall and with a second lid retention means in the back wall, and
   (b) the lid is a rectangularly shaped, perforated plate with a first lid locking means connected to the lid upper surface along its front edge and a second lid locking means connected to said upper surface along its back edge.

5. The tissue cassette of claim 4 wherein the first lid locking means is a locking ridge extending upwardly from the upper surface of the lid and the second lid locking means is one or more locking fingers extending upwardly from said lid upper surface.

6. The tissue cassette of claim 5 wherein the lid further includes a handle mounted along the lid back edge and coplanar with the lid.

7. The tissue cassette of claim 5 wherein the lid further includes a lid back wall along the lid back edge, a first lid side wall extending slightly recessed from and along one lid side edge from the locking ridge to the back edge, and a second lid side wall extending slightly recessed from and along the other lid side edge from the locking ridge to the back edge, said lid walls all connected to and extending upwardly from the lid upper surface.

8. The tissue cassette of claim 5 wherein the lid further includes one or more guides extending upwardly from said lid upper surface along the back edge of the lid.

9. The tissue cassette of claim 5 further including one or more recessed slots which extend partially into the inner surface of the back wall and pass through the base to form a drain thereto.

10. The tissue cassette of claim 5 wherein the second lid retention means is one or more recesses in the outer surface of the back wall wherein said recesses are each aligned with and matingly retain a corresponding locking finger when the tissue cassette is in the closed position.

11. The tissue cassette of claim 10 further including a first angled wall connected to the front wall.

12. The tissue cassette of claim 11 wherein the front wall extends from the top edge of the side walls only a short distance downwardly along the side walls and forms the first lid retention means which matingly retains the locking ridge when the tissue cassette is in the closed position, and the first angled wall is connected along the bottom edge of the front wall and extends downwardly and outwardly therefrom.

13. The tissue cassette of claim 12 wherein the side walls extend outwardly beyond the front wall and connect to the side edges of the first angled wall.

14. The tissue cassette of claim 12 wherein the bottom terminates behind and beneath the front wall and forms a front edge and includes a second angled wall connected to the bottom along said front edge, said second angled wall extending outwardly and upwardly therefrom toward the front wall and terminating short of the front wall, thereby forming an opening between the front wall and the second angled wall.

15. The tissue cassette of claim 14 wherein the second angled wall includes a plurality of perforations therethrough.

16. The tissue cassette of claim 11 wherein the front wall is connected to the bottom along the bottom front edge and extends upwardly therefrom to the top edge of the side walls, said front wall including a longitudinal slot extending therethrough forming the second lid retention means which matingly retains the locking ridge when the tissue cassette is in the closed position, and the first angled wall is connected along the bottom of the front wall and extends upwardly and outwardly therefrom.

17. The tissue cassette of claim 16 wherein the side walls extend outwardly beyond the front wall and connect to the side edges of the second angled wall.

18. The tissue cassette of claim 11 wherein the first angled wall has a textured outer surface.

19. The tissue cassette of claim 1, 2, 3, 4, 5, 10, or 11 wherein the base, the lid and the gates are molded as a unitary structure from a plastic material which has a low flexural modulus and a tendency to break when flexed and which is resistant to tissue specimen processing chemicals.

20. Apparatus for holding a tissue specimen during processing comprising:

(a) an open-topped rectangular base with a perforated bottom, a back wall, a front wall, and a pair of side walls extending upwardly from and connected to the bottom along its outside edges, a longitudinal slot extending through the front wall, one or more recesses in the outer surface of the back wall, one or more recessed slots in the inner surface of the back wall and passing through the bottom, and an angled wall connected to the bottom of the front wall and extending upwardly and outwardly therefrom, (b) a rectangular, perforated lid of the same approximate dimensions as the base, a locking ridge connected to the upper surface of the lid along its front edge, wherein said locking ridge matingly engages the longitudinal slot in the front wall when the lid is positioned on the base, and one or more locking fingers mounted to the upper surface of the lid along its back edge, wherein said locking fingers correspond in number with and matingly engage the recesses when the lid is positioned on the base, and (c) one or more gates joining the lid to the base in an open position wherein said gates will break when flexed.

21. Apparatus for holding a tissue specimen during processing comprising:

(a) an open-topped, rectangular base with a perforated bottom, a back wall and a pair of side walls extending upwardly from and connected to the bottom along its outside edges, a front wall connected between the side walls and extending a short distance down the side walls toward the bottom, one or more recesses in the outer surface of the back wall, one or more recessed slots in the inner surface of the back wall and passing through the bottom, and a first angled wall connected to the bottom of the front wall and extending downwardly and outwardly therefrom, said bottom extending from the back wall and terminating behind and beneath the front wall and including a second angled wall connected along the front edge of the bottom and extending upwardly and outwardly toward the front wall but terminating short of the front wall to form an opening therebetween, (b) a rectangular, perforated lid of the same approximate dimensions as the rectangular base, a locking ridge mounted to the upper surface of the lid along its front edge, wherein said locking ridge matingly engages the bottom of the front wall when the lid is positioned on the base, and one or more locking fingers mounted to the upper surface of the lid along its back edge, wherein said locking fingers correspond in number with and matingly engage the recesses when the lid is positioned on the base, and (c) one or more gates joining the lid to the base in an open position wherein said gates will break when flexed.

* * * * *